United States Patent

Muehl et al.

[11] Patent Number: 5,985,897
[45] Date of Patent: Nov. 16, 1999

[54] BENZOTHIPHENE COMPOUNDS, INTERMEDIATES, COMPOSITIONS, AND METHODS

[76] Inventors: Brian Stephen Muehl, 940 Country La., Indianapolis, Ind. 46217; Alan David Palkowitz, 10737 Kingsmill Dr., Carmel, Ind. 46032

[21] Appl. No.: 08/956,087

[22] Filed: Oct. 23, 1997

Related U.S. Application Data

[60] Provisional application No. 60/029,519, Oct. 24, 1996.

[51] Int. Cl.$^6$ ....................... A61K 31/445; C07D 409/12
[52] U.S. Cl. ....................... 514/324; 514/212; 514/223.5; 514/442; 514/443; 540/596; 544/146; 546/202; 548/525; 549/51
[58] Field of Search ..................... 546/202; 548/525; 549/51; 544/146; 540/596; 514/212, 324, 233.5, 442, 443

[56] References Cited

U.S. PATENT DOCUMENTS

| | | | |
|---|---|---|---|
| 3,394,125 | 7/1968 | Crenshaw | 548/525 |
| 3,413,305 | 11/1968 | Crenshaw | 548/525 |
| 4,133,814 | 1/1979 | Jones et al. | 546/202 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,395,842 | 3/1995 | Labrie | 514/320 |
| 5,470,854 | 11/1995 | Angerer et al. | 514/233 |
| 5,472,962 | 12/1995 | Koizumi et l. | 514/233.5 |
| 5,484,795 | 1/1996 | Bryant et al. | 514/319 |
| 5,723,474 | 3/1998 | Palkowitz | 514/324 |

FOREIGN PATENT DOCUMENTS

| | | |
|---|---|---|
| 062 503 | 10/1982 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem.* 14(12):1185–1190 (1971).
Jones, C.D., et al, *J. Med. Chem.* 27: 1057–1066) 1984.
Jones, C.D., et al, *J. Med. Chem.* 35: 931–938 1992.

*Primary Examiner*—Ceila Chang

[57] ABSTRACT

The invention provides benzothiophene compounds, formulations, and methods of inhibiting bone loss or bone resorption, particularly osteoporosis, and cardiovascular-related pathological conditions, including hyperlipidemia, and estrogen-dependent cancer.

21 Claims, No Drawings

BENZOTHIPHENE COMPOUNDS, INTERMEDIATES, COMPOSITIONS, AND METHODS

This application claims the benefit of U.S. Provisional Application Ser. No. 60/029,519 filed Oct. 24, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases effecting both women, and to a lesser extent men. Cancer cells of this type are dependent on a source of estrogen to maintain the orginal tumor as well as to proliferate and metastasize to other locations. The most common forms of estrogen dependent cancer are breast and uterine carcinomas. Current chemotherapy of these diseases relies primarily on the use of anti-estrogens, predominately tamoxifen. The use of tamoxifen, although efficaceous, is not without undesirable side-effects, for example, estrogen agonist properties, such as uterine hypertrophy and carcinogenic potential. Compounds of the current invention while showing the same or better potential for anti-cancer activity, also demonstrate a lower potential for estrogen agonist activity.

In response to the clear need for new pharmaceutical agents which are capable of alleviating the symptoms described herein, the instant invention provides benzo[b] thiophene compounds, pharmaceutical formulations, and methods of using said compounds for the inhibition of the disease states as indicated herein.

SUMMARY OF THE INVENTION

The present invention relates to compounds of formula

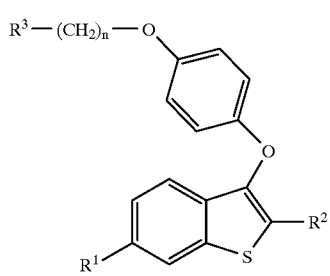

I wherein $R^1$ is —H, —OH, —O($C_1$–$C_4$ alkyl), —OCO($C_1$–$C_6$ alkyl), —O(CO)O($C_1$–$C_6$ alkyl), —OCOAr, —O(CO) OAr, where Ar is phenyl or optionally substituted phenyl, or —OSO$_2$($C_2$–$C_6$ alkyl);

$R^2$ is $C_1$–$C_5$ n-alkyl, $C_3$–$C_6$ branched alkyl, $C_3$–$C_7$ cycloalkyl, $C_3$–$C_6$ alkenyl, $C_4$–$C_7$ cycloalkenyl, or $C_3$–$C_5$ alkynyl;

n is 2 or 3; and

R³ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt or solvate thereof.

The instant invention further relates to pharmaceutical formulations containing compounds of formula I, and the use of said compounds at least for the inhibition of bone loss or bone resorption, particularly osteoporosis, and cardiovascular-related pathological conditions, including hyperlipidemia, and estrogen-dependent cancer.

The present invention still further relates to compounds of formula II, which are useful as intermediates in the synthesis of compounds of formula I:

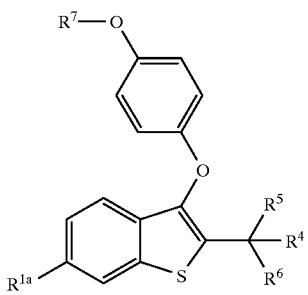

II wherein:
R$^{1a}$ is —H or —OR$^8$, where R$^8$ is a hydroxy-protecting group;

R$^4$ is —OH or —H;

R$^5$ and R$^6$ are, independently, —H, C$_1$–C$_4$ n-alkyl, C$_3$–C$_5$ branched alkyl, C$_2$–C$_5$ alkenyl, C$_2$–C$_4$ alkynyl, or R$^5$ and R$^6$ may be taken together with methylene groups or vinyl groups to form 3 to 7-membered cycloalkyl or cycloalkenyl rings; and R$^7$ is —OH or —OR$^9$, where R$^9$ is a hydroxy-protecting group which can be selectively removed in the presence of R$^8$.

DETAILED DESCRIPTION OF THE INVENTION

General terms used in the description of compounds herein described bear their usual meanings. For example, the term, "C$_1$–C$_6$ alkyl" refers to aliphatic carbon chains containing 1 to 6 carbon atoms, these chains may be either straight or branched. The term, "C$_1$–C$_5$ n-alkyl" refers to straight aliphatic chains of 1 to 5 carbon atoms including methyl, ethyl, n-propyl, n-butyl, and n-pentyl. The term, "C$_3$–C$_6$ branched alkyl" refers to branched aliphatic chains of 3 to 6 carbon atoms, for example, 2-propyl, 2-butyl, 3-butyl, and the like. The term "C$_3$–C$_6$ alkenyl" refers to a hydrocarbon chain of 3 to 6 carbon atoms which contains at least one carbon-carbon double bond, for example, 3-propenyl, 4-butenyl, 4-(3-methyl)butenyl, 3,5-pentadiene, and the like. The term "C$_3$–C$_7$ cycloalkyl" refers to aliphatic carbon rings with 3–7 carbon atoms, such as cyclopropyl, cyclohexyl, and the like. The term "C$_4$–C$_7$ cycloalkenyl" refers to hydrocarbon rings of 4–7 carbon atoms, which contain at least one carbon-carbon double bond, for example, 2-cyclobutene, 3-cyclohexene, 2,4-cyclohexyldiene, and the like.

Included within the scope of the present invention are compounds which contain asymmetric carbon centers. Those compounds may therefore exist in stereoisomeric forms. The present invention includes each of the stereoisomers, mixtures thereof, or racemic mixtures, which are all useful for the pharmacologic properties described herein. Similarly, alkenyl compounds of the present invention may exist as geometric isomers (cis/trans; Z/E). The present invention includes each of the geometric isomers and mixtures thereof, which are useful for the pharmacologic properties described herein.

Similarly, the term "—OC$_1$–C$_4$ alkyl" represents a C$_1$–C$_4$ alkyl group attached through an oxygen, such as, for example, methoxy, ethoxy, n-propoxy, isopropoxy, and the like. Of these C$_1$–C$_4$ alkoxy groups, methoxy is highly preferred.

The term "substituted phenyl" refers to a phenyl group having one or more substituents selected from the group consisting of C$_1$–C$_4$ alkyl, —OC$_1$–C$_4$ alkyl, hydroxy, nitro, chloro, fluoro, or tri(chloro or fluoro)methyl.

The term "hydroxy-protecting group" contemplates numerous functionalities used in the literature to protect a hydroxyl function during a chemical sequence and which can be removed to yield the phenol. Included within this group are acyls, mesylates, tosylates, benzyl, alkylsilyloxys, C$_1$–C$_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred hydroxy protecting groups, particularly methyl, are essentially as described in the Examples, infra.

The term "leaving group" means a chemical entity which is capable of being displaced by an amino function via an SN$_2$ reaction. Such reactions are well known in the art and such groups would include halogens, mesylates, tosylates, and the like. A preferred leaving group is bromo.

The term "inhibit" includes its generally accepted meaning which includes prohibiting, preventing, restraining, and slowing, stopping, or reversing progression, severity, or ameliorating a resultant symptom or effect.

The term "solvate" represents an aggregate that comprises one or more molecules of the solute, such as a formula I compound, with one or more molecules of solvent.

The compounds of formula I are derivatives of benzo[b] thiophene which is named and numbered according to the Ring Index, The American Chemical Society, as follows:

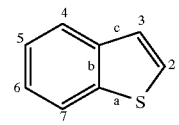

Compounds of formula I include 3-[4-[2-(1-pyrrolidinyl) ethoxy]phenoxy]-2-cyclohexylbenzo[b] thiophene hydrochloride;

3-[4-[2-(1-hexamethyleneimino)ethoxy]phenoxy]-2-cyclohexylbenzo[b]thiophene hydrochloride;

3-[4-[3-(1-piperidinyl)propoxy]phenoxy]-2-cyclohexylbenzo[b] thiophene hydrochloride;

3-[4-[2-(1-piperidinyl)ethoxy]phenoxy]-2-cyclohexyl-6-methoxybenzo[b]thiophene hydrochloride;

3-[4-[2-(1-piperidinyl)ethoxy]phenoxy]-2-cyclohexyl-6-hydroxybenzo[b]thiophene;

3-[4-[2-(1-piperidinyl)ethoxy]phenoxy]-2-cyclohexy-6-hydroxylbenzo[b]thiophene hydrochloride;

3-[4-[2-(1-piperidinyl)ethoxy]phenoxy]-2-propenyl-6-hydroxylbenzo[b]thiophene hydrochloride;

3-[4-[2-(1-piperidinyl)ethoxy]phenoxy]-2-(3-methylbut-1-yl)-6-hydroxylbenzo[b]thiophene hydrochloride;

3-[4-[2-(1-piperidinyl)ethoxy]phenoxy]-2-(2-methylbut-1-yl)-6-hydroxylbenzo[b]thiophene hydrochloride;

3-[4-[2-(1-piperidinyl)ethoxy]phenoxy]-2-(1-cyclohexyl-2-ene)-6-hydroxylbenzo[b]thiophene hydrochloride;

3-[4-[2-(1-piperidinyl)ethoxy]phenoxy]-2-(1-cyclohexyl-2,4-diene)-6-hydroxylbenzo[b]thiophene hydrochloride;

3-[4-[2-(1-piperidinyl)ethoxy]phenoxy]-2-(3-methylpent-3-ene-1-yl)-6-hydroxylbenzo[b]thiophene hydrochloride;

3-[4-[2-(1-piperidinyl)ethoxy]phenoxy]-2-cyclohexyl-6-acetoxylbenzo[b]thiophene hydrochloride;

3-[4-[2-(1-piperidinyl)ethoxy]phenoxy]-2-cyclohexyl-6-benzoyloxylbenzo[b]thiophene hydrochloride;

3-[4-[2-(1-piperidinyl)ethoxy]phenoxy]-2-cyclohexyl-6-n-butylsulfonoyloxylbenzo[b]thiophene hydrochloride;

3-[4-[2-(1-piperidinyl)ethoxy]phenoxy]-2-n-pentyl-6-n-butylsulfonoyloxylbenzo[b]thiophene hydrochloride;

3-[4-[2-(1-pyrrolidinyl)ethoxy]phenoxy]-2-cyclopentyl-6-n-butylsulfonoyloxylbenzo[b]thiophene hydrochloride;

3-[4-[2-(1-piperidinyl)ethoxy]phenoxy]-2-cyclohexyl-6-acetoxylbenzo[b]thiophene hydrochloride;

3-[4-[2-(1-piperidinyl)ethoxy]phenoxy]-2-cyclohexyl-6-butoyloxylbenzo[b]thiophene hydrochloride;

3-[4-[2-(1-piperidinyl)ethoxy]phenoxy]-2-cycloheptyl-6-acetoxylbenzo[b]thiophene hydrochloride;

3-[4-[2-(1-piperidinyl)ethoxy]phenoxy]-2-(cyclohex-3-ene-1-yl)-6-acetoxylbenzo[b]thiophene hydrochloride; and the like.

Preferred embodiments of the current invention are those compounds wherein n is two and $R_3$ is piperidinyl.

Several synthetic pathways are available for preparing the compounds of the instant invention. One synthetic route in the synthesis of compounds of formula I wherein $R^1$ is —H employs as starting material a compound of formula III. The compound of formula III and the synthesis of same is provided in U.S. Pat. No. 5,488,058, the disclosure of which is herein incorporated by reference.

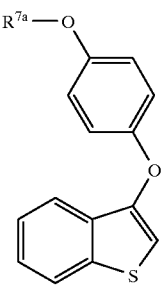

III wherein $R^{7a}$ is $R^9$ with its previous meaning.

The first steps in the present process for the conversion of compounds of formula III to the compounds of the present invention involve the metallation of a compound of formula III at the 2-position. Although other alkali metals may be used, for example, Na, K, and the like, the preferred metal is lithium. Thus, a compound of formula III is converted to the 2-lithio derivative to provide a compound of formula IV. A compound of formula IV, which is formed as an intermediate and not isolated due to its instability, is reacted with a ketone of formula $R^5R^6CO$ to provide a tertiary alcohol of formula IIa, wherein $R^5$ and $R^6$ are as previously defined. The alcohol is then reduced to provide a 2-alkyl derivative of formula IIc. Alternatively, and particularly when $R_2$ is $C_1$–$C_5$ n-alkyl or $C_3$–$C_5$ straight chain alkenyl, a compound of formula IV is alkylated with an appropriate alkyl or alkenyl halide to provide a compound of formula IIb directly. This synthetic sequence is illustrated in Scheme I, below.

Scheme I

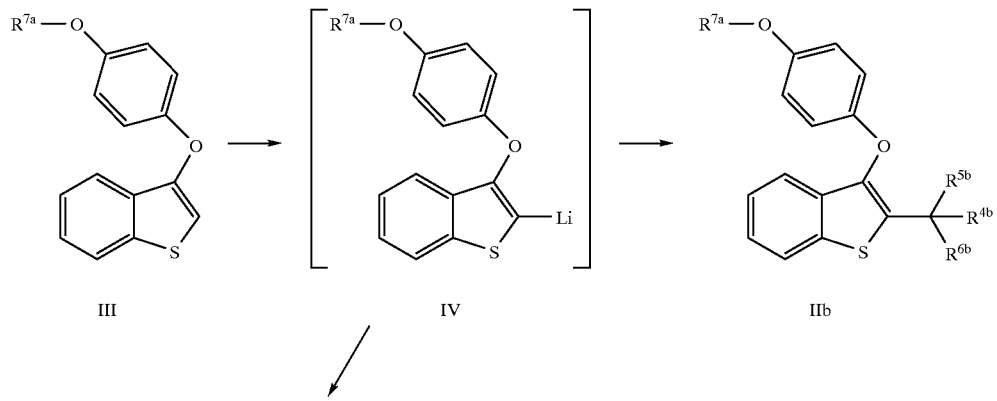

III          IV          IIb

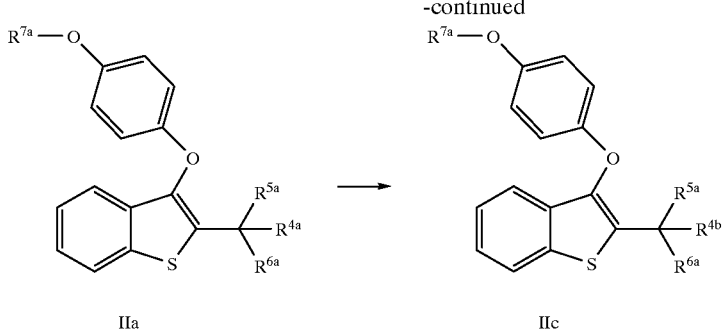

wherein: $R^{7a}$ is as previously defined;
$R^{4a}$ is —OH;
$R^{4b}$ is —H;
$R^{5a}$ is $R^5$;
$R^{5b}$ is —H;
$R^{6a}$ is $R^6$, wherein $R^6$ is a previously defined; and
$R^{6b}$ is $C_0$–$C_4$ n-alkyl or $C_2$–$C_5$ alkenyl.

In the first step of Scheme I, a compound of formula III is treated with a slight excess of n-butyllithium in hexanes, in an appropriate solvent and under an inert atmosphere such as nitrogen. Appropriate solvents include an inert solvent or mixtures of solvents, such as, for example, diethyl ether, dioxane, and tetrahydrofuran (THF). Of these, tetrahydrofuran, and particularly anhydrous THF, is preferred.

The present reaction optimally is run at a temperature from about −78° C. to about 25° C. and the reaction time is usually less than thirty minutes.

As mentioned previously, the intermediate compound of formula IV is not isolated, but is instead used directly in the next reaction by the addition of the next reagent to the reaction mixture.

Compounds of formula IIb (where $R^2$ is $C_1$–$C_5$ n-alkyl or $C_3$–$C_5$ straight chain alkenyl) are synthesized directly from a compound of formula IV by the addition of the appropriate $C_1$–$C_5$ alkyl halide or a $C_3$–$C_5$ straight chain alkenyl halide. The halide may be chloro, bromo, or iodo, with the preferred halide being bromo. The halide is usually dissolved in an inert solvent (the same solvent used to generate a compound of formula IV) and added directly to the reaction mixture used to generate the intermediate compound of formula IV. The reaction, if cold initially, is allowed to warm to ambient temperature and the reaction time is then between one and three hours. The final product (a compound of formula IIb) may be isolated by standard methods and purified by chromatography and/or crystallization. The compounds of formula IIa and IIc may be also prepared from the intermediate IV.

After generating a compound of formula IV, a ketone of $R^5COR^6$ dissolved in the same solvent used to generate IV, is added directly and in a dropwise fashion to the reaction mixture. If the reaction mixture is cold, the reaction is allowed to warm to ambient temperature and the reaction time is between one to three hours. The final product (IIa) may be isolated by standard methods and purified by chromatography and/or crystallization.

The tertiary alcohol IIa resulting from the addition of a ketone to the 2-lithio derivative (IV) is reduced to the alkane by treatment with triethylsilane/triflouroacetic acid in an inert halogenated solvent, such as dichloromethane, chloroform, and the like. This reaction is optimally run between −10 and 20° C., and usually requires 0.5–3 h for completion. The product of this reaction, a compound of formula IIc is isolated by standard chromatographic techniques.

Compounds of formula I wherein $R^1$ is not —H may be derived from compounds of formula IId, which are synthesized starting from compounds of formula V by the route shown in Schemes II and III, below.

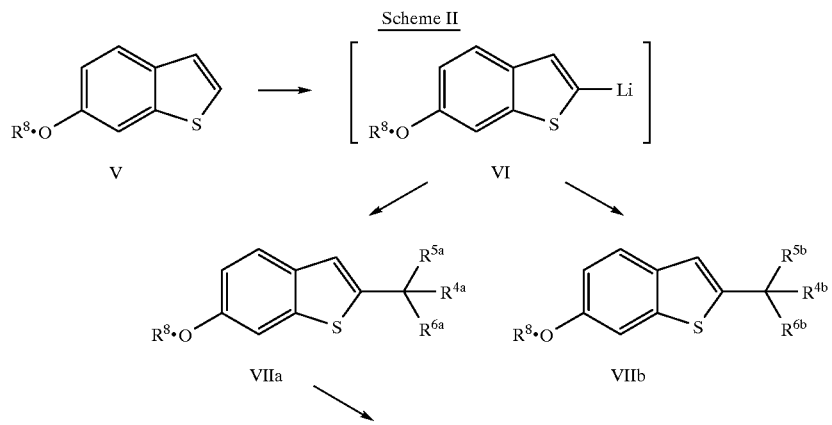

Scheme II

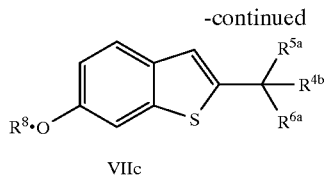

VIIc wherein $R^{4a}$, $R^{4b}$, $R^{5a}$, $R^{5b}$, $R^{6a}$, $R^{6b}$, and $R^8$ have their previous meanings.

Compounds of formula V may be obtained by methods provided, supra. Both $R^8$ and $R^9$ are hydroxy-protecting groups. These protecting groups must have different chemical properties from each other, for example, $R^9$ must be able to be removed in the presence of $R^8$ (when present) without its removal. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965).

Because carbon-carbon, non-aromatic, multiple bonds are often susceptible to reduction by the hydrogenation process used to remove a protecting group such as a benzyl group, for the synthesis of compounds of formula I where $R^2$ is alkenyl, cycloalkenyl, or alkynyl, a benzyl group for $R^8$ or $R^9$ is not preferred.

For the synthesis of compounds of formula I where $R^2$ is alkyl or cycloalkyl, a preferred protecting group for $R^8$ (when present) is a methyl group, and a preferred protecting group for $R^9$ is a benzyl group. Thus, a preferred compound of formula V is 6-methoxybenzo[b]thiophene for the synthesis of this subset of the compounds of formula I.

For the synthesis of compounds of formula I where $R^2$ is alkenyl, cycloalkenyl, or alkynyl, a preferred protecting group for $R^8$ (when present) is also a methyl group, but a preferred protecting group for $R^9$ is a sulfonate, such as methylsulfonate.

The chemistry ulitized in the synthesis of compounds of formula VIIa, VIIb, and VIIc is directly analogous to that used in Scheme I to synthesize compounds of formula IIa, IIb, and IIc. The same reaction conditions, reagents, and preferences are applicable.

Compounds of formula VIIb-c are converted to the 3-ether linked compounds of formula IId in the following manner. Compounds of formula VII are brominated at the 3-position (VIII), and then reacted with a 4-(hydroxy-protected)phenol via an Ullman reaction to produce compounds of formula IId. This transformation is illustrated in Scheme III, below.

Scheme III

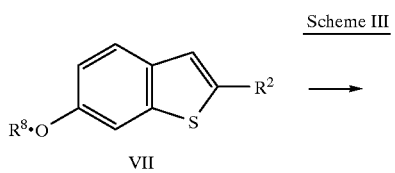

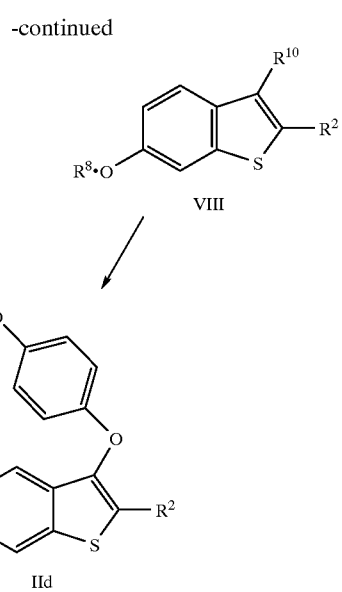

wherein $R^2$ and $R^8$ have their previous meanings, $R^{10}$ is a leaving group, and $R^9$ is benzyl if $R^2$ is alkyl or cycloalkyl, or $R^9$ is methylsulfonate if $R^2$ is alkenyl, cycloalkenyl, or alkynyl.

In the first step of Scheme III, an appropriate leaving group is selectively placed at the 3-position of the formula VII starting material via standard procedures. Appropriate $R^{10}$ leaving groups include sulfonates such as methanesulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as bromo, chloro, and iodo, and other related leaving groups. However, to insure proper placement of the leaving group, the named halogens are preferred, and bromo is especially preferred.

The present reaction is carried out using standard procedures. For example, when the preferred halogenating agents are used, an equivalent of such a halogenating agent, preferably bromine, is reacted with an equivalent of the formula VII substrate, in the presence of a suitable solvent, such as chloroform or acetic acid. The reaction is run at a temperature from about 40° C. to about 80° C. and is usually complete in one to six hours.

The reaction product from the above process step, a compound of formula VIII, is then reacted with either 4-benzyloxyphenol or 4-methanesulfonyloxyphenol to form compounds of formula IId The 4-benzyloxyphenol and 4-methanesulfonyloxyphenol are known compounds which are commericially available, or which can be prepared via standard procedures. This coupling reaction is known as an Ullman-type reaction and is run according to standard procedures [See, for example, *Advanced Organic Chemistry: Reactions, Mechanisms, and Structure*, Fourth Edition, 3–16, (J. March, ed., John Wiley & Sons, Inc. 1992); Jones, C. D., *J. Chem. Soc. Perk. Trans. I*, 4:407 (1992)].

In general, equivalent amounts of the two aryl substrates, in the presence of up to an equimolar amount of a copper(I) oxide catalyst and an appropriate solvent, are heated to reflux under an inert atmosphere. Preferably, an equivalent of a formula IV compound in which $R^9$ is bromo is reacted with an equivalent amount of 4-benzyloxyphenol in the presence of an equivalent amount of cuprous oxide.

Appropriate solvents for this reaction are those solvents or mixture of solvents which remain inert throughout the reaction. Typically, organic bases, particularly a hindered base, such as, for example, 2,4,6-collidine, are preferred solvents.

The temperature employed in this step should be sufficient to effect completion of this coupling reaction, and will influence the amount of time required therefor. When the reaction mixture is heated to reflux under an inert atmosphere such as nitrogen, the time-to-completion usually will be from about 20 to about 60 hours.

The compounds of formula IIb-d are converted to the corresponding phenol, for example, where $R^7$ is hydroxyl, in preparation of adding the basic side-chain of the final products of formula I. Illustrated in Scheme VI is the selective deprotection of the $R^9$ group, where $R^9$ is a benzyl protecting group in the presence of the $R^8$ (when present) protecting group. Illustrated in Scheme VIa is the selective deprotection of the $R^{9a}$ group, where $R^{9a}$ is a methanesulfonyl protecting group in the presence of the $R^8$ (when present) protecting group.

Scheme IV

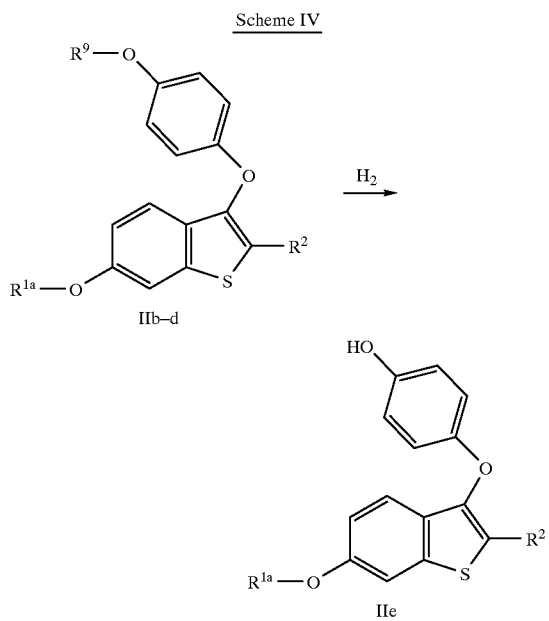

When $R^9$ is the benzyl moiety, $R^{1a}$ is hydrogen, or $R^8(R^{1a})$ is methyl, the present process step is carried out via standard hydrogenation procedures. Typically, the formula IIa–d substrate is added to a suitable solvent or mixture of solvents, followed by the addition of a proton donor to accelerate the reaction and an appropriate hydrogenation catalyst. Appropriate catalysts include noble metals and oxides such as palladium, platinum, and rhodium oxide on a support such as carbon or calcium carbonate. Of these, palladium-on-carbon, and particularly 10% palladium-on-carbon, is preferred.

Solvents for this reaction are those solvents or mixture of solvents which remain inert throughout the reaction. Typically, ethylacetate and $C_1-C_4$ aliphatic alcohols, particularly ethanol, is preferred. For the present reaction, hydrochloric acid serves as an adequate and preferred proton donor.

When run at ambient temperature and hydrogen pressure ranging from about 30 psi to about 50 psi, the present reaction runs quite rapidly. Progress of this reaction may be monitored by standard chromatographic techniques, such as thin layer chromatography.

Scheme IVa

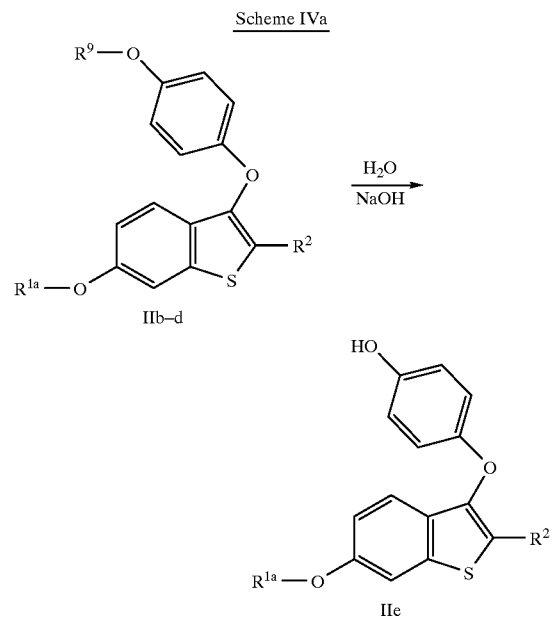

When $R^{9a}$ is the methanesulfonyl moiety, $R^{1a}$ is hydrogen, or $R^8(R^{1a})$ is methyl, the present process step is carried out via standard hydrolysis procedures. Hydrolysis of a sulfonate is most commonly done under basic conditions. The substrate is dissolved in solvent mixture of water, THF, and/or $C_1-C_4$ alcohols, with the preferred being ethanol-water (75:25)(v/v). A strong base is added, such as NaOH, $Na_2CO_3$, KOH, and the like, with the preferred being 1N NaOH. Usually a molar excess (2–5 fold) of the base is utilized to speed the reaction to completion. The reaction is run at temperatures of 25°–150° C., with the preferred being the reflux temperature of the above solvent mixture. The reaction is usually complete within one to ten hours. However, the progress of the reaction may be monitored by tlc and the like. The final product is further isolated by standard techniques, such as chromatography and/or crystallization.

Compounds of formula IIa–e are included within the definition of compounds of formula II, which are useful for preparing the pharmaceutically active compounds of formula I.

Examples of compounds of formula II include:
3-(4-Benzyloxy)phenoxy-2-(1-hydroxycyclohex-2-ene-1-yl)benzo[b]thiophene;
3-(4-Benzyloxy)phenoxy-2-(1-cyclohex-3-ene)benzo[b]thiophene;
3-(4-Benzyloxy)phenoxy-2-(1-hydroxycyclohex-2,4-diene-1-yl)benzo[b]thiophene;
3-(4-Benzyloxy)phenoxy-2-(1-cyclohex-2,4-diene)benzo[b]thiophene;
3-(4-Hydroxy)phenoxy-2-(1-cyclohex-2,4-diene)benzo[b]thiophene;

3-(4-Benzyloxy)phenoxy-2-(1-hydroxycyclopent-1-yl)benzo[b]thiophene;

3-(4-Benzyloxy)phenoxy-2-(1-cyclopentyl)benzo[b]thiophene;

3-(4-Hydroxyl)phenoxy-2-(1-cyclopentyl)benzo[b]thiophene;

3-(4-Benzyloxy)phenoxy-2-(1-hydroxy-n-pentyl-1-yl)benzo[b]thiophene;

3-(4-Benzyloxy)phenoxy-2-(1-hydroxy-2-methylbut-1-yl)benzo[b]thiophene;

3-(4-Benzyloxy)phenoxy-2-(1-hydroxy-3-methylbut-1-yl)benzo[b]thiophene;

3-(4-Benzyloxy)phenoxy-2-(1-hydroxy-4-methylbut-1-yl)benzo[b]thiophene;

3-(4-Benzyloxy)phenoxy-2-(1-hydroxy-2-methylprop-1-yl)benzo[b]thiophene;

3-(4-Benzyloxy)phenoxy-2-(1-hydroxypent-3-ene-1-yl)benzo[b]thiophene;

3-(4-Benzyloxy)phenoxy-2-(1-hydroxyhex-2,4-diene-1-yl)benzo[b]thiophene;

3-(4-Hydroxy)phenoxy-2-(1-hydroxy-n-pentyl-1-yl)benzo[b]thiophene;

3-(4-Hydroxy)phenoxy-2-(1-hydroxy-2-methylbut-1-yl)benzo[b]thiophene;

3-(4-Hydroxy)phenoxy-2-(1-hydroxy-3-methylbut-1-yl)benzo[b]thiophene;

3-(4-Hydroxy)phenoxy-2-(1-hydroxy-4-methylbut-1-yl)benzo[b]thiophene;

3-(4-Hydroxy)phenoxy-2-(1-hydroxy-2-methylprop-1-yl)benzo[b]thiophene;

3-(4-Hydroxy)phenoxy-2-(1-hydroxypent-3-ene-1-yl)benzo[b]thiophene;

3-(4-Hydroxy)phenoxy-2-(1-hydroxyhex-2,4-diene-1-yl)benzo[b]thiophene;

3-(4-Benzyloxy)phenoxy-2-(1-hydroxy-n-pentyl-1-yl)-6-methoxybenzo[b]thiophene;

3-(4-Hydroxy)phenoxy-2-(1-hydroxy-2-methylbut-1-yl)-6-methoxybenzo[b]thiophene;

3-(4-Benzyloxy)phenoxy-2-(1-hydroxy-3-methylbut-1-yl)-6-methoxybenzo[b]thiophene;

3-(4-Hydroxy)phenoxy-2-(1-hydroxy-4-methylbut-1-yl)-6-methoxybenzo[b]thiophene;

3-(4-Benzyloxy)phenoxy-2-(1-hydroxy-2-methylprop-1-yl)-6-methoxybenzo[b]thiophene;

3-(4-Hydroxy)phenoxy-2-(1-hydroxypent-3-ene-1-yl)-6-methoxybenzo[b]thiophene;

3-(4-Benzyloxy)phenoxy-2-(1-hex-2,4-dieneyl)-6-methoxybenzo[b]thiophene; and the like.

The next reaction sequence in the synthesis of the compounds of formula I, which involves the addition of the basic side-chain on the phenolic hydroxyl of the IIe compounds. This may be accomplished by one of two different methods. The first method is illustrated in Scheme V, below.

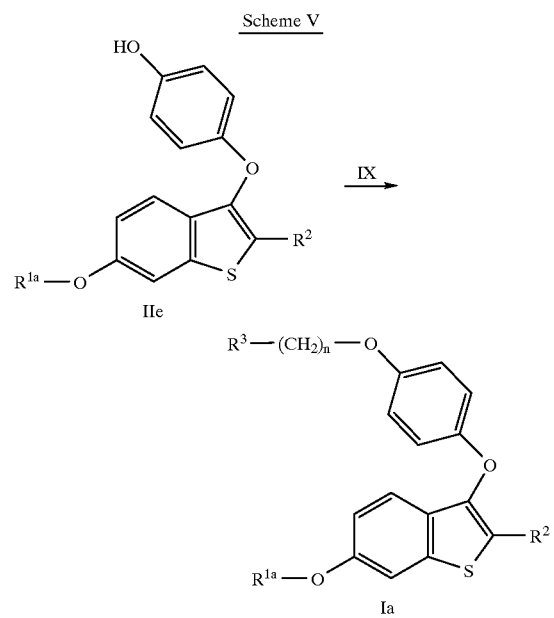

Scheme V wherein $R^{1a}$, $R^2$, $R^3$, and n have their previous meanings

Upon preparation of a formula IIe compound, it is reacted with a compound of formula IX $$R^3—(CH^2)_n—Q \qquad\qquad IX$$

wherein $R^3$ and n are as defined above, and Q is a leaving group, such as bromo or, preferably, chloro, to form a compound of formula Ia.

In the process shown in Scheme V, the alkylation is carried out via standard procedures. Compounds of formula IX are commercially available or are prepared by means well known to one of ordinary skill in the art. Preferably, the hydrochloride salt of a formula IX compound, particularly 2-chloroethylpiperidine hydrochloride, is used.

Generally, at least about 1 equivalent of formula IIe substrate are reacted with 2 equivalents of a formula IX compound in the presence of at least about 4 equivalents of an alkali metal carbonate, for example, $K_2CO_3$, $Na_2CO_3$, and the like, preferably cesium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Typically, ambient temperature is sufficient and preferred.

The present reaction preferably is run under an inert atmosphere, particularly nitrogen.

Under the preferred reaction conditions, this reaction will run to completion in about 16 to about 20 hours. The progress of the reaction is typically monitored via standard chromatographic techniques.

In an alternative method for preparing compounds of formula Ia, a formula IIe compound is reacted with an excess of an alkylating agent of the formula X. This alternate reaction is illustrated in Scheme VI, below.

Scheme VI

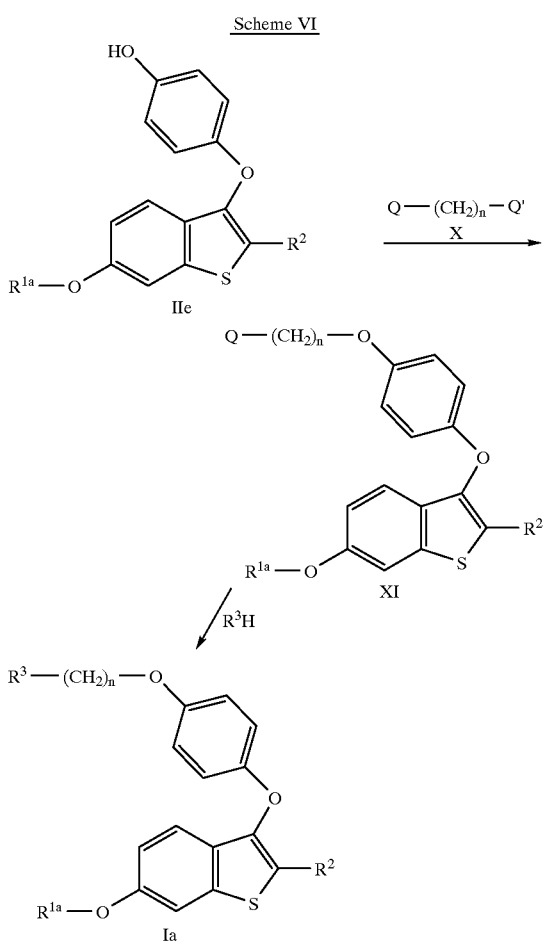

wherein $R^{1a}$, $R^2$, $R^3$, and n have their previous meanings, and Q and Q' each are the same or different leaving groups.

Appropriate leaving groups for compound X would be mesylate, tosylate, chloro, bromo, and the like, with the preferred being the di-bromo (Q and Q' are bromo). A preferred compound for X is 1,2-dibromoethane.

The first step of this sequence, the alkylation reaction, is run with a several fold (2–5) molar excess of compound X in an alkaline solution to form the intermediate compounds of formula XI. Subsequently, formula XI compounds are treated with the secondary amines ($R^3H$), which displaces the leaving group Q, thus providing compounds of formula Ia.

A preferred alkali solution for this alkylation reaction contains potassium carbonate in an inert solvent such as, for example, methyethyl ketone (MEK) or DMF. In this solution, the 4-hydroxy group of the benzoyl moiety of a formula IIe compound exists as a phenoxide ion which displaces one of the leaving groups (Q') of the alkylating agent (X).

An alkali solution containing the reactants and reagents is typically brought to reflux and allowed to run to completion. When using MEK as the preferred solvent, reaction times run from about 6 hours to about 20 hours.

The reaction product (XI) from this step is then reacted with 1-piperidine, 1-pyrrolidine, methyl-1-pyrrolidine, dimethyl-1-pyrrolidine, 4-morpholine, dimethylamine, diethylamine, diisopropylamine, or 1-hexamethyleneimine, via standard techniques, to form compounds of formula Ia.

In general, a molar excess (1–2 fold), of the secondary amine is used to drive the reaction to completion in a timely manner. Preferably, the hydrochloride salt of piperidine is reacted with the alkylated compound of formula XI in an inert solvent, such as anhydrous DMF, THF, MEK, and the like, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run for completion. The progress of this reaction step is typically monitored via standard chromatographic techniques.

A formula Ia compound may be deprotected to form a phenolic compound of formula Ib. Compounds of Ib may subsequently be acylated or sulfonated on the 6-hydroxyl function to provide compounds of formula Ic. This reaction sequence is illustrated in Scheme VII, below.

Scheme VII

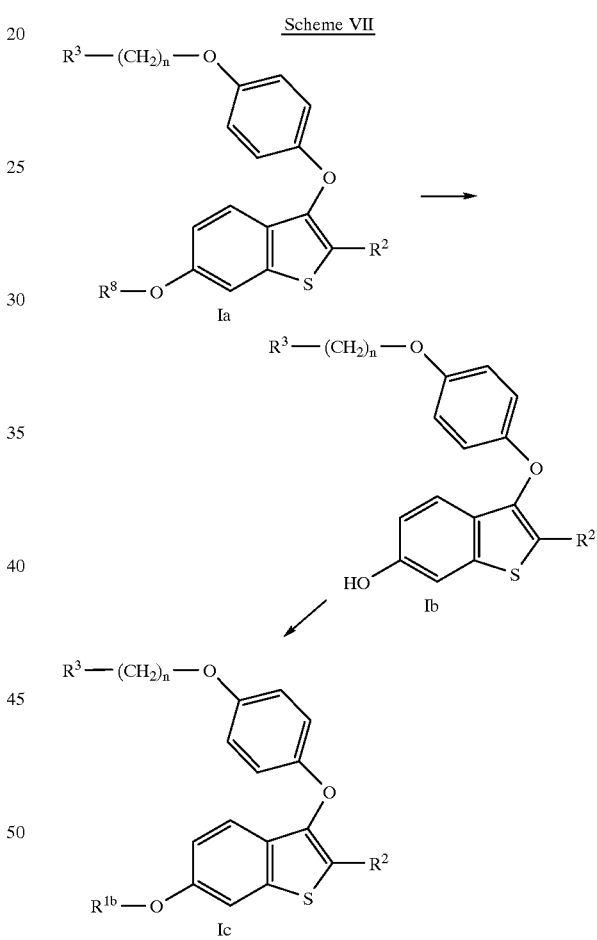

wherein $R^{1b}$ is —$OCOC_6H_5$, —$OCO(C_1-C_6$ alkyl), —$O(CO)O(C_1-C_6$ alkyl), or —$OSO_2(C_4-C_6$ alkyl), $R^8$ is methyl, and $R^2$, $R^3$, and n have their previous meanings.

The first step of this final sequence is the removal of the $R^8$ hydroxy-protecting group, yielding a compound of formula Ib. This may be accomplished in a variety of ways depending on the nature of the protecting group (see: references, supra). A preferred protecting group is a methoxy (where $R^8$ is methyl), which is used to illustrate the following sequence. The 6-methoxy of Ia is converted to the hydroxyl by cleavage with Lewis acids, such as $AlCl_3$, $BBr_3$, and the like. Examples of the reaction conditions for this de-protection step is found in U.S. Pat. Nos. 4,133,814 and 4,418,068, the disclosures of which are herein incorporated by reference.

Compounds of formula Ic are prepared by replacing the 6-hydroxy moiety, when present, with a moiety of the formula —O—CO—($C_1$-$C_6$ alkyl), —O—CO-phenyl, or —O—$SO_2$—($C_4$-$C_6$ alkyl) using well known procedures (see, for example, U.S. Pat. Nos. 5,393,763 or 5,482,949, the disclosures of which are herein incorporated by reference).

For example, when an —O—CO($C_1$-$C_6$ alkyl) or —O—CO-phenyl group is desired, the hydroxy compound of formula Ib is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, for example, Haslam et al., *Tetrahedron*, 36:2409–2433 (1980).

The present reactions are carried out at moderate temperatures, in the range from about −25° C. to about 100° C., frequently under an inert atmosphere such as nitrogen gas. However, ambient temperature is usually adequate for the reaction to run.

Acylation of a 6-hydroxy group is also performed by acid-catalyzed reactions of the appropriate carboxylic acids in inert organic solvents. Acid catalysts such as sulfuric acid, polyphosphoric acid, methanesulfonic acid, and the like are used.

When a formula Ic compound is desired in which the 6-hydroxy group of a formula Ib compound is converted to a group of the formula —O—$SO_2$—($C_2$-$C_6$ alkyl), the hydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The hydroxy compounds also can be reacted with the appropriate sulfonic anhydride or mixed sulfonic anhydrides. Such reactions are carried out under conditions provided above in the discussion of reactions with acid halides and the like.

The compounds of formula Ia–c are included in the definition of compounds of formula I, and are useful for the pharmacologic properties as described herein.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions, including hyperlipidemia.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to inhibit the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof for at least one month, or more typically for six months, or chronically.

The instant invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed, infra. The instant invention contemplates and encompasses such maladies although not specified by name.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
|---|---|
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
|---|---|
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
|---|---|
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
|---|---|
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
|---|---|
| Active Ingredient | 0.1–1000 mg |
| Sodium carboxymethyl cellulose | 50 mg |
| Syrup | 1.25 mL |

-continued

| Ingredient | Weight |
| --- | --- |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Preparations and Examples are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1
3-(4-Benzyloxy)phenoxybenzo[b]thiophene

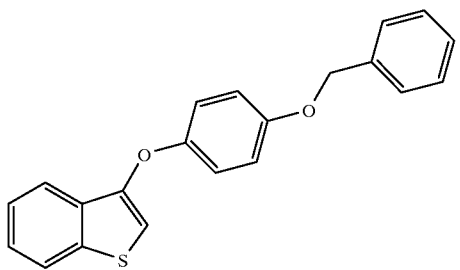

To a solution of 3-bromo-benzo[b]thiophene (69.62 g, 0.325 mol) in 55 mL of anhydrous 2,4,6-collidine under $N_2$ is added 4-benzyloxyphenol (97.6 g, 0.488 mol) and cuprous oxide (23.3 g, 0.163 mol). The mixture is heated to reflux for 24 hours. Upon cooling, the reaction mixture is diluted with ethyl acetate (200 mL) and the crude mixture is filtered through a pad of Celite® (Aldrich, Milwaukee, Wis.) to remove inorganic salts. The filtrate is washed with 1N hydrochloric acid (3×150 mL). The organic is dried (sodium sulfate) and concentrated in vacuo to a liquid. Thianaphthene was removed by distillation (10 mm Hg, 115–120° C.). The remainder of the material is chromatographed (silicon dioxide, hexanes: ethyl acetate 85:15) to provide 12.2 g of benzo[b]thiophene and 12.95 g (35% based on recovered starting material) of 3-(4-benzyloxy) phenoxybenzo[b]thiophene as an off-white solid.

mp 84–86° C.; PNMR ($CDCl_3$) δ 7.91–7.83 (m, 2H), 7.47–7.34 (m, 7H), 7.04 (q, $J_{AB}$=9.0 Hz, 4H), 6.47 (s, 1H), 5.07 (s, 2H).; Anal. Calcd. for $C_{21}H_{16}O_2S$: C, 75.88; H, 4.85. Found: C, 75.75; H, 5.00.

Example 1
3-[(4-benzyloxy)phenoxy]-2-(2-hydroxyprop-2-yl) benzo[b]thiophene

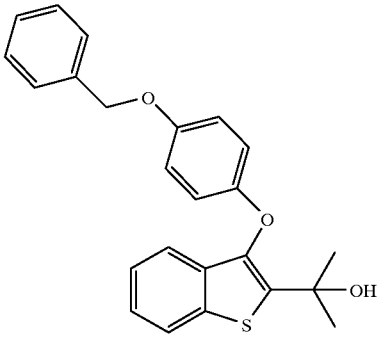

To a solution of 3-(4-benzyloxy)phenoxybenzo[b] thiophene (3.0 g, 9.0 mmol) in anhydrous THF (100 ml) at –78° C. is added n-butyl lithium (7.5 ml of 1.6 M solution in hexanes, 11.7 mmol) dropwise. After stirring for 20 min at –78° C., acetone (1.32 ml, 18.0 mmol) is added. The resulting solution is slowly warmed to room temperature. Sat. $NaHCO_3$ solution (100 ml) was added and the resulting mixture is extracted with EtOAc (3×). The combined organic layers are washed with sat. NaCl solution (2×), dried ($Na_2SO_4$), and concentrated in vacuo. The resulting oil is purified by chromatography ($SiO_2$, EtOAc/hexanes) to give 2.69 g (77%) of 3-(4-benzyloxy)phenoxy)-2-(2-hydroxyprop-2-yl)benzo[b]thiophene as a brown oil.

PNMR ($CDCl_3$) δ 7.76 (d, J=7.0 Hz, 1H), 7.40–7.21 (m, 9H), 6.88 (m, 3H), 5.01 (s, 2H), 2.66 (s, 1H), 1.71 (s, 6H). FD mass spec: 390.; Anal. Calcd. for $C_{24}H_{22}O_3S$: C, 73.82; H, 5.68. Found: C, 73.99; H, 5.80.

Example 2
3-[(4-Benzyloxy)phenoxy]-2-(isopropyl)benzo[b] thiophene

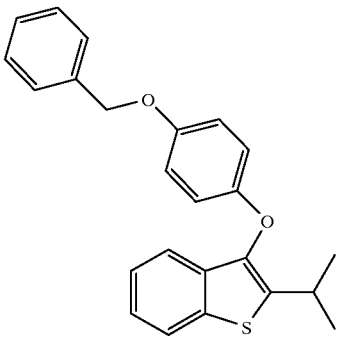

To a solution of 3-[(4-benzyloxy)phenoxy]-2-(2-hydroxyprop-2-yl)benzo[b]thiophene (4.25 g, 11.0 mmol) in $CH_2Cl_2$ (100 ml) at 0° C. is added triethylsilane (5.24 ml, 33.0 mmol). After stirring for 20 min at 0° C., trifluoroacetic acid (51 ml, 0.66 mol) is added. The resulting solution is stirred for 40 min at 0° C., then poured into ice water. The layers are separated, and the organic washed with sat. $NaHCO_3$ solution (2×). The organic is dried ($Na_2SO_4$) and concentrated in vacuo to an oil. The crude product is purified by chromatography (SiO$_2$, EtOAc/hexanes) to give 2.40 g (58%) of 3-(4-benzyloxy)phenoxy)-2-(isopropyl)benzo[b]thiophene as an orange oil.

PNMR (CDCl$_3$) δ 7.76 (d, J=7.8 Hz, 1H), 7.46–7.22 (m, 9H), 6.87 (s, 3H), 5.02 (s, 2H), 3.42 (m, 1H), 1.32 (d, J=6.9 Hz, 6H). FD mass spec: 374.; Anal. Calcd. for C$_{24}$H$_{22}$O$_2$S: C, 76.97; H, 5.92. Found: C, 77.28; H, 6.10.

Example 3

3-[(4-Hydroxy)phenoxy]-2-isopropylbenzo[b]thiophene

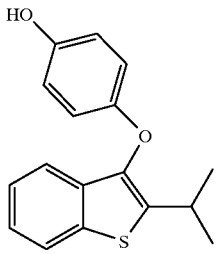

To a solution of 3-[(4-benzyloxy)phenoxy]-2-isopropylbenzo[b]thiophene (2.40 g, 6.40 mmol) in 1:1 EtOH/EtOAc in a Parr bottle is added 10% Pd/C (1.0 g). To this suspension is added 1.0 mL of con. HCl. The resulting mixture is hydrogenated at 40 psi for 20 min. The reaction is filtered through Celite®, and the filtrate is concentrated in vacuo to an oil. The crude product is partitioned between CHCl$_3$ and sat. NaHCO$_3$ solution. The layers are separated, and the organic is dried (Na$_2$SO$_4$) and concentrated in vacuo to give 1.7 g (93%) of 3-(4-hydroxy)phenoxy)-2-(isopropyl)benzo[b]thiophene as a brown oil.

PNMR (CDCl$_3$) δ 7.76 (d, J=7.7 Hz, 1H), 7.44 (m, 1H), 7.49–7.30 (m, 2H), 6.82–6.70 (m, 4H), 4.83 (br s, 1H), 3.41 (m, 1H), 1.31 (d, J=6.7 Hz, 6H).; FD mass spec: 284.; Anal. Calcd. for C$_{17}$H$_{16}$O$_2$S: C, 71.80; H, 5.67. Found: C, 72.02; H, 5.71.

Example 4

3-[4-[2-(1-Piperidinyl)ethoxy]phenoxy]-2-(2-propyl]benzo[b]thiophene Hydrochloride

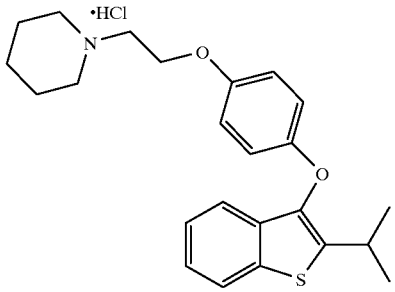

To a solution of 3-[(4-hydroxy)phenoxy]-2-(isopropyl)benzo[b]thiophene (1.71 g, 6.0 mmol) in 100 mL of anhydrous DMF is added finely ground anhydrous K$_2$CO$_3$ (8.30 g, 60 mmol) and 2-chloroethylpiperidine (1.54 g, 9.0 mmol). The resulting solution is stirred under N$_2$ at room temperature for 16 h. The reaction is then partitioned between EtOAc and H$_2$O. The layers are separated and the organic is washed several times with H$_2$O. The organic is dried (Na$_2$SO$_4$) and concentrated in vacuo to an oil that is chromatographed (SiO$_2$, 0–5% CH$_3$OH/CHCl$_3$) to provide [3-[4-[2-(1-piperidinyl)ethoxy]phenoxy]-2-(isopropyl]benzo[b]thiophene as a brown oil. This material is treated with Et$_2$OoHCl to provide 1.27 g (54%) of [3-[4-[2-(1-piperidinyl)ethoxy]phenoxy]-2-(isopropyl]benzo[b]thiophene hydrochloride as a white solid.

mp 168–170° C.; PNMR (CDCl$_3$) δ 7.75 (d, J=7.0 Hz, 1H), 7.35–7.23 (m, 3H), 6.86–6.77 (m, 4H), 4.52–4.49 (m, 2H), 3.66–3.62 (m, 2H), 3.41–3.33 (m, 3H), 3.00–2.80 (m, 2H), 2.46–2.30 (m, 2H), 1.90–2.05 (m, 3H), 1.53 (m, 1H), 1.30 (d, J=6.7 Hz, 6H).; FD mass spec: 395.; Anal. Calcd. for C$_{24}$H$_{29}$NO$_2$So1.0 HCl: C, 66.72; H, 7.00; N, 3.24. Found: C, 67.00; H, 7.05; N, 3.07.

Example 5

3-(4-Benzyloxy)phenoxy)-2-(3-propenyl)benzo[b]thiophene

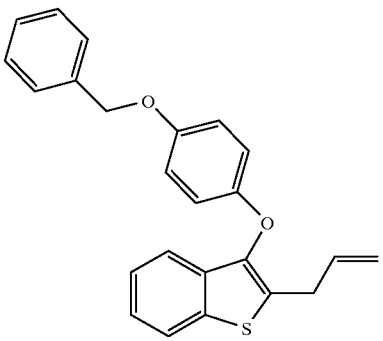

To a solution of 3-[(4-benzyloxy)phenoxy] benzo[b]thiophene (2.0 g, 6.0 mmol) in anhydrous THF (100 ml) at −78° C. is added n-butyllithium (4.9 mL, 1.6M solution in hexanes, 7.8 mmol) dropwise. After 20 min at −78° C. allylbromide (1.04 ml, 12.0 mmol) is added. The solution is allowed to slowly warm to room temperature then sat. NaHCO$_3$ soln.(100 mL) is added. The mixture is extracted with EtOAc, and the organic is dried (Na$_2$SO$_4$), and concentrated in vacuo to an oil. The crude product is purified by chromatography (SiO$_2$, EtOAc/hexanes) to give 1.95 g (87%) of 3-(4-benzyloxy)phenoxy)-2-(3-propenyl)benzo[b]thiophene as a yellow oil.

PNMR (CDCl$_3$) δ 7.75 (d, J=7.3 Hz, 1H), 7.60–7.35 (m, 9H), 6.88 (s, 3H), 6.05 (m, 1H), 5.30–5.15 (m, 2H), 5.03 (s, 2H), 3.56 (d, J=6.6 Hz, 2H).; FD mass spec: 372.; Anal. Calcd. for C$_{24}$H$_{20}$O$_2$S: C, 77.39; H, 5.41.

Example 6

3-[4-Hydroxy)phenoxy]-2-propylbenzo[b]thiophene

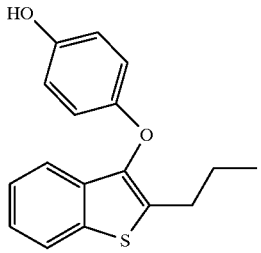

In a manner similar to that used in Example 3, 3-[4-methoxy)phenoxy]-2-propylbenzo[b]thiophene is converted to the title compound in 97% yield, isolated as a tan oil.

PNMR (CDCl$_3$) δ 7.73 (d, J=7.3 Hz, 1H), 7.50 (m, 1H), 7.40–7.33 (m, 2H), 6.90–6.80 (m, 4H), 2.78 (t, J=7.7 Hz, 2H), 1.67 (dd, J=14.9, 7.4 Hz, 2H), 0.97 (t, J=7.4 Hz, 3H).; FD mass spec: 284.

Example 7

3-[4-[2-(1-Piperidinyl)ethoxy]phenoxy]-2-propylbenzo[b]thiophene Hydrochloride

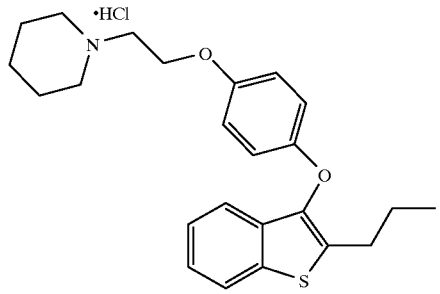

In a manner similar to that used in Example 4, 3-[4-hydroxy)phenoxy]-2-propylbenzo[b]thiophene and 2-chloroethylpiperidine are converted to the title compound in 38% yield and is isolated as a white amorphous solid, mp 142–144° C.

PNMR (CDCl$_3$) δ 7.40 (d, J=7.2 Hz, 1H), 7.47–7.30 (m, 3H), 6.82 (ABq, J=9.1 Hz, J=17.8 Hz, 4H), 4.50 (br s, 2H), 3.80–3.70 (m, 2H), 3.37 (br s, 2H), 2.82–2.76 (m, 4H), 2.50–2.30 (m, 2H), 2.10–1.90 (m, 3H), 1.90–1.75 (m, 2H), 1.52 (m, 1H), 0.96 (t, J=7.3 Hz, 3H).; FD mass spec: 396.; Anal. Calcd. for C$_{24}$H$_{29}$NO$_2$So1.0 HCl: C, 66.72; H, 7.00; N, 3.24. Found: C, 66.51; H, 7.16; N, 3.32.

Example 8

3-(4-Benzyloxy)phenoxy-2-(1-hydroxycyclohex-1-yl)benzo[b]thiophene

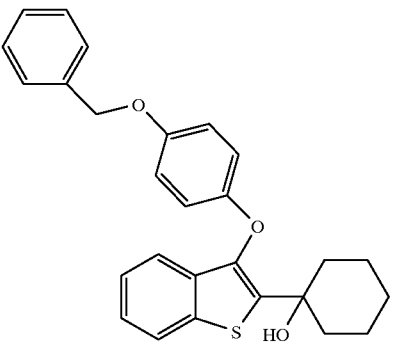

In a manner similar to that used in Example 1, 3-(4-benzyloxy) phenoxybenzo[b]thiophene and cyclohexanone are converted to the title compound in 77% yield and isolated as a brown oil.

PNMR (CDCl$_3$) δ 7.76 (d, J=8 Hz, 1H), 7.60–7.26 (m, 9H), 6.89 (s, 3H), 5.01 (s, 2H), 2.56 (s, 1H), 2.23–2.03 (m, 4H), 1.95–1.66 (m, 6H).; FD mass spec: 430.; Anal. Calcd. for C$_{27}$H$_{26}$O$_3$S: C, 75.32; H, 6.09. Found: C, 75.11; H, 5.94.

Example 9

3-(4-Benzyloxy)phenoxy-2-cyclohexylbenzo[b]thiophene

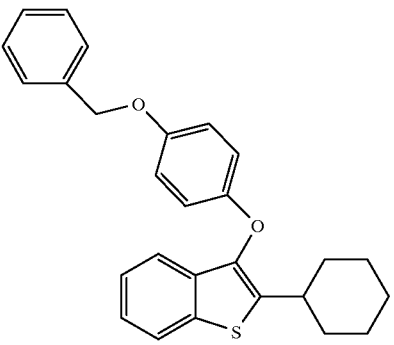

In a manner similar to that used in Example 2, 3-(4-benzyloxy)phenoxy-2-(1-hydroxycyclohex-1-yl)benzo[b]thiophene is converted to the title compound in 58% yield and isolated as a white amorphous solid.

PNMR (CDCl$_3$) δ 7.75 (d, J=7.0 Hz, 1H), 7.56–7.26 (m, 9H), 6.87 (s, 3H), 5.01 (s, 2H), 3.07 (m, 1H), 2.13–2.02 (m, 2H),; 1.95–1.85 (m, 3H), 1.60–1.30 (m, 5H).; FD mass spec: 414.; Anal. Calcd. for C$_{27}$H$_{26}$O$_2$S: C, 78.23; H, 6.32. Found: C, 78.10; H, 6.32.

Example 10

3-(4-Hydroxy)phenoxy-2-cyclohexylbenzo[b]thiophene

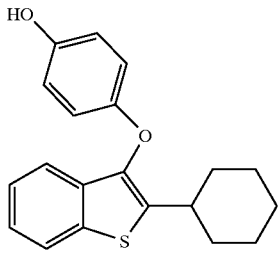

In a manner similar to that used in Example 3, 3-(4-benzyloxy)phenoxy-2-cyclohexylbenzo[b]thiophene is converted to the title compound in 94% yield and is isolated as a brown oil. PNMR (CDCl$_3$) δ 7.75 (d, J=8.5 Hz, 1H), 7.35–7.22 (m, 3H), 6.83–6.70 (m, 4H), 4.74 (br s, 1H), 3.05 (m, 1H), 2.13–2.10 (m, 2H), 1.95–1.76 (m, 3H), 1.65–1.30 (m, 5H).; FD mass spec: 324.; Anal. Calcd. for C$_{20}$H$_{20}$O$_2$S: C, 74.04; H, 6.21. Found: C, 73.89; H, 6.06.

Example 11

3-[4-[2-(1-Piperidinyl)ethoxy]phenoxy]-2-cyclohexylbenzo[b]thiophene Hydrochloride

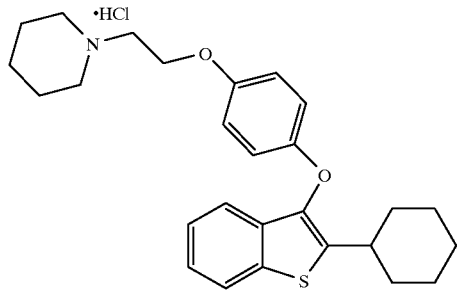

In a manner similar to that used in Example 4, 3-(4-hydroxy)phenoxy-2-cyclohexylbenzo [b] thiophene an 2-chloroethylpiperidine is converted to the title compound in 85% yield and is isolated as a white amorphous powder.

PNMR (CDCl$_3$) δ 7.74 (d, J=8.0 Hz, 1H), 7.32–7.22 (m, 3H), 6.87–6.78 (m, 4H), 4.52 (s, 2H), 3.80–3.66 (m, 2H), 3.53–3.40 (m, 2H), 3.15 (m, 1H), 3.00–2.83 (m, 2H), 2.50–2.30 (m, 2H), 2.10–1.80 (m, 9H), 1.65–1.30 (m, 5H).; FD mass spec: 435.; Anal. Calcd. for C$_{27}$H$_{33}$NO$_2$S·1.0 HCl: C, 68.69; H, 7.26; N, 2.97. Found: C, 68.46; H, 7.40; N, 3.19.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.70° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine:xylazine (2:1, V:V) mixture and a blood sample was collected by cardiac puncture. The animals were then sacrificed by asphyxiation with CO$_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH–8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol (EE$_2$; an orally available form of estrogen), and rats treated with certain compounds of the instant invention. Although EE$_2$ caused a decrease in serum cholesterol when orally administered at 0.1 mg/kg/day, it also exerted a stimulatory action on the uterus so that EE$_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound No. | Dose mg/kg[a] | Uterine Weight % Inc[b] | Uterine Eosinophil (Vmax)[c] | Serum Cholest. % Dec.[d] |
|---|---|---|---|---|
| EE2[e] | 0.1 | 159.0* | 212.4* | 76.6* |
| Example 4 | 0.1 | 8.0 | 3.0 | -27.6 |
|  | 1.0 | 29.7* | 4.5 | 19.2 |
|  | 10.0 | 41.0* | 12.0 | 61.6* |
| Example 7 | 0.1 | 10.3 | 4.2 | -11.1 |
|  | 1.0 | 52.0* | 4.8 | 41.2* |
|  | 10.0 | 37.2* | 4.5 | 46.6* |
| Example 11 | 0.1 | 36.8* | 4.5 | 55.8* |
|  | 1.0 | 45.4* | 5.4 | 58.9* |
|  | 10.0 | 30.6* | 4.8 | 50.2* |

[a]mg/kg PO
[b]Uterine Weight % increase versus the ovariectomized controls
[c]Eosinophil peroxidase Vmaxium
[d]Serum cholesterol decrease versus ovariectomized controls
[e]17-α-Ethynyl-estradiol
*p < .05

In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl β-cyclodextrin are orally administered to test animals. Distal femur metaphysis and proximal tibiae data are compared to intact and ovariectomized test animals. Results are reported as percent protection relative to ovariectomy.

Ovariectomy of the test animals causes a significant reduction in femur density compared to intact, vehicle treated controls. Orally administered ethynyl estradiol ($EE_2$) prevents this loss, but the risk of uterine stimulation with this treatment is ever-present.

In accordance with the above procedures, compounds of the present invention and ethynyl estradiol ($EE_2$) in 20% hydroxypropyl β-cyclodextrin are orally administered to test animals. Distal femur metaphysis data compares intact and ovariectomized test animals. Results are reported as the mean±the standard error of the mean.

Estrogen Dependent Breast Cancer: MCF-7 Proliferation Assay Test Procedure

MCF-7 breast adenocarcinoma cells (ATCC HTB 22) are maintained in MEM (minimal essential medium, phenol-red free, Sigma St.Louis Mo.) supplemented with 10% fetal bovine serum (FBS) (v/v), L-glutamine (2 mM), sodium pyruvate (1 mM), HEPES (10 mM), non-essential amino acids and bovine insulin (1 ug/mL). Ten days prior to the assay, the MCF-7 cells are switched to maintenance medium supplemented with 10% dextrancoated charcoal stripped fetal bovine serum (DCC-FBS) assay medium in place of the 10% FBS to deplete internal stores of estrogen. MCF-7 cells are removed from the maintenance flasks using a cell dissociating medium (Ca/Mg free HBSS (phenol-red free) supplemented with 10 mM HEPES and 2 mM EDTA. Cells are washed twice with the assay medium and adjusted to 80,000 cells/mL. Approximately 100 μL (8,000 cells) are added to a flat-bottomed microculture well (Costar 3596) and incubated at 37° C. in a 5% $CO_2$ humidified incubator for 48 hours to allow cell adherence and equilibrium after transfer. Serial dilutions of the compounds of formula I or DMSO as a diluent control are prepared in assay medium and 50 μL transferred to triplicate microcultures followed by 50 μL of assay medium for a final volume of 200 μL. After an additional 48 hours of incubation, the microcultures are pulsed with tritiated thymidine (1 μCi/well) for 4 hours. Culture are terminated by freezing at -70° C. for 24 hours followed by thawing and harvesting of microcultures using a Skatron Semiautomatic Cell Harvester. Samples are counted by liquid scintillation. Fifty percent inhibitory concentration of the test drugs ($IC_{50}$) are determined versus the control (DMSO).

Results are calculated and expressed as $IC_{50}$, for example, that concentration of the drug which inhibits the growth of the MCF-7 cells by 50%.

Compounds of the present invention are active in this experimental model as seen below in Table 2.

TABLE 2

| Compound | $IC_{50}$ |
|---|---|
| Example 4 | 30 |
| Example 7 | 30 |
| Example 11 | 15 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. orally administered compounds are either dissolved or suspended in 0.2 mL corn oil. Each treatment, including acacia and corn oil control treatments, is administered once daily to each test animal. Following the initial tumor measurement and selec-

We claim:
1. A compound of formula I:

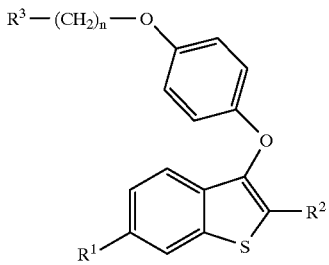

wherein
R¹ is —H, —OH, —O(C₁–C₄ alkyl), —OCO(C₁–C₆ alkyl), —O(CO)O(C₁–C₆ alkyl), —OCOAr, —O(CO)OAr, where Ar is phenyl or optionally substituted phenyl, or —OSO₂ (C₂–C₆ alkyl);
R² is C₁–C₅ n-alkyl, C₃–C₆ branched alkyl, C₃–C₇ cycloalkyl, C₃–C₆ alkenyl, C₄–C₇ cycloalkenyl, or C₃–C₅ alkynyl;
n is 2 or 3; and
R³ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt or solvate thereof.

2. A compound according to claim 1 wherein R¹ is —H.
3. A compound according to claim 1 wherein R² is C₁–C₅ n-alkyl, C₃–C₆ branched alkyl, or C₃–C₇ cycloalkyl.
4. A compound according to claim 1 wherein R¹ is —OH.
5. A compound according to claim 4 wherein R² is C₁–C₅ n-alkyl, C₃–C₆ branched alkyl, or C₃–C₇ cycloalkyl.
6. A compound according to claim 1 wherein R² is cyclohexyl.
7. A compound according to claim 1 wherein n is two.
8. A compound according to claim 7 wherein R³ is pyrrolidinyl, piperidinyl, or hexamethyleneimino.
9. A compound according to claim 1 wherein R¹ is hydrogen, R² is cyclohexyl, R³ is piperidinyl, n is two, and said salt thereof is the hydrochloride salt.
10. A compound according to claim 1 wherein R¹ is hydrogen, R² is 2-propyl, R³ is piperidinyl, n is two, and said salt thereof is the hydrochloride salt.
11. A compound according to claim 1 wherein R¹ is hydrogen, R² is propyl, R³ is piperidinyl, n is two, and said salt thereof is the hydrochloride salt.
12. A pharamceutical composition comprising a compound according to claim 1 with a pharmaceutically acceptable carrier, diluent, or excipient.
13. A compound according to claim 1 selected from the group consisting of
3-[4-[2-(1-pyrrolidinyl)ethoxy]phenoxy]-2-cyclohexylbenzo[b]thiophene hydrochloride;
3-[4-[2-(1-hexamethyleneimino)ethoxy]phenoxy]-2-cyclohexylbenzo[b]thiophene hydrochloride;
3-[4-[3-(1-piperidinyl)propoxy]phenoxy]-2-cyclohexylbenzo[b]thiophene hydrochloride;
3-[4-[2-(1-piperidinyl)ethoxy]phenoxy]-2-cyclohexyl-6-methoxybenzo[b] thiophene hydrochloride;
3-[4-[2-(1-piperidinyl)ethoxy]phenoxy]-2-cyclohexyl-6-hydroxybenzo[b]thiophene;
3-[4-[2-(1-piperidinyl)ethoxy]phenoxy]-2-cyclohexy-6-hydroxylbenzo[b]thiophene hydrochloride;
3-[4-[2-(1-piperidinyl)ethoxy]phenoxy]-2-propenyl-6-hydroxylbenzo[b]thiophene hydrochloride;
3-[4-[2-(1-piperidinyl)ethoxy]phenoxy]-2-(3-methylbut-1-yl)-6-hydroxylbenzo[b]thiophene hydrochloride;
3-[4-[2-(1-piperidinyl)ethoxy]phenoxy]-2-(2-methylbut-1-yl)-6-hydroxylbenzo[b]thiophene hydrochloride;
3-[4-[2-(1-piperidinyl)ethoxy]phenoxy]-2-(1-cyclohexyl-2-ene)-6-hydroxylbenzo[b]thiophene hydrochloride;
3-[4-[2-(1-piperidinyl)ethoxy]phenoxy]-2-(1-cyclohexyl-2,4-diene)-6-hydroxylbenzo[b]thiophene hydrochloride;
3-[4-[2-(1-piperidinyl)ethoxy]phenoxy]-2-(3-methylpent-3-ene-1-yl)-6-hydroxylbenzo[b]thiophene hydrochloride;
3-[4-[2-(1-piperidinyl)ethoxy]phenoxy]-2-cyclohexyl-6-acetoxylbenzo[b]thiophene hydrochloride;
3-[4-[2-(1-piperidinyl)ethoxy]phenoxy]-2-cyclohexyl-6-benzoyloxylbenzo[b]thiophene hydrochloride;
3-[4-[2-(1-piperidinyl)ethoxy]phenoxy]-2-cyclohexyl-6-n-butylsulfonoyloxylbenzo[b]thiophene hydrochloride;
3-[4-[2-(1-piperidinyl)ethoxy]phenoxy]-2-n-pentyl-6-n-butylsulfonoyloxylbenzo[b]thiophene hydrochloride;
3-[4-[2-(1-pyrrolidinyl)ethoxy]phenoxy]-2-cyclopentyl-6-n-butylsulfonoyloxylbenzo[b]thiophene hydrochloride;
3-[4-[2-(1-piperidinyl)ethoxy]phenoxy]-2-cyclohexyl-6-acetoxylbenzo[b]thiophene hydrochloride;
3-[4-[2-(1-piperidinyl)ethoxy]phenoxy]-2-cyclohexyl-6-butoyloxylbenzo[b]thiophene hydrochloride;
3-[4-[2-(1-piperidinyl)ethoxy]phenoxy]-2-cycloheptyl-6-acetoxylbenzo[b]thiophene hydrochloride; and
3-[4-[2-(1-piperidinyl)ethoxy]phenoxy]-2-(cyclohex-3-ene-1-yl)-6-acetoxylbenzo[b]thiophene hydrochloride.

14. A method of inhibiting bone loss or bone resorption which comprises administering to a patient in need thereof an effective amount of a compound of claim 1.
15. A method according to claim 14, wherein said bone loss or bone resorption is due to menopause or ovariectomy.
16. A method of lowering serum cholesterol levels which comprises administering to a patient in need thereof an effective amount of a compound of claim 1.
17. A method of inhibiting estrogen-dependent cancer which comprises administering to a patient in need thereof an effective amount of a compound of claim 1.
18. A method according to claim 17 wherein said estrogen-dependent cancer is breast cancer.
19. A method according to claim 17 wherein said estrogen-dependent cancer is uterine cancer.
20. A compound of formula II:

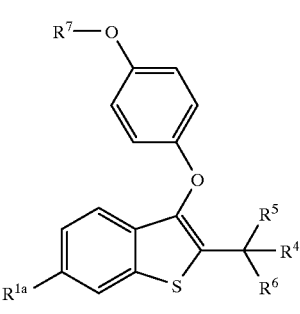

wherein:
- $R^{1a}$ is —H or —$OR^8$, where $R^8$ is a hydroxy-protecting group;
- $R^4$ is —OH or —H;
- $R^5$ and $R^6$ are, independently, —H, $C_1$–$C_4$ n-alkyl, $C_3$–$C_5$ branched alkyl, $C_2$–$C_5$ alkenyl, $C_2$–$C_4$ alkynyl, or $R^5$ and $R^6$ may be taken together with methylene groups or vinyl groups to form 3 to 7-membered cycloalkyl or cycloalkenyl rings; and
- $R^7$ is —OH or —$OR^9$, where $R^9$ is a hydroxy-protecting group which can be selectively removed in the presence of $R^8$; with the proviso that only two of $R^4$, $R^5$, and $R^6$ can be hydrogen.

21. A compound according to claim 20 selected from the group consisting of
3-(4-Benzyloxy)phenoxy-2-(1-hydroxycyclohex-2-ene-1-yl)benzo[b]thiophene;
3(4-Benzyloxy)phenoxy-2-(1-cyclohex-3-ene)benzo[b]thiophene;
3(4-Benzyloxy)phenoxy-2-(1-hydroxycyclohex-2,4-diene-1-yl)benzo[b]thiophene;
3(4-Benzyloxy)phenoxy-2-(1-cyclohex-2,4-diene)benzo[b]thiophene;
3(4-Hydroxy)phenoxy-2-(1-cyclohex-2,4-diene)benzo[b]thiophene;
3(4-Benzyloxy)phenoxy-2-(1-hydroxycyclopent-1-yl)benzo[b]thiophene;
3(4-Benzyloxy)phenoxy-2-(1-cyclopentyl)benzo[b]thiophene;
3(4-Hydroxyl)phenoxy-2-(1-cyclopentyl)benzo[b]thiophene;
3(4-Benzyloxy)phenoxy-2-(1-hydroxy-n-pentyl-1-yl)benzo[b]thiophene;
3(4-Benzyloxy)phenoxy-2-(1-hydroxy-2-methylbut-1-yl)benzo[b]thiophene;
3(4-Benzyloxy)phenoxy-2-(1-hydroxy-3-methylbut-1-yl)benzo[b]thiophene;
3(4-Benzyloxy)phenoxy-2-(1-hydroxy-4-methylbut-1-yl)benzo[b]thiophene;
3(4-Benzyloxy)phenoxy-2-(1-hydroxy-2-methylprop-1-yl)benzo[b]thiophene;
3(4-Benzyloxy)phenoxy-2-(1-hydroxypent-3-ene-1-yl)benzo[b]thiophene;
3(4-Benzyloxy)phenoxy-2-(1-hydroxyhex-2,4-diene-1-yl)benzo[b]thiophene;
3(4-Hydroxy)phenoxy-2-(1-hydroxy-n-pentyl-1-yl)benzo[b]thiophene;
3(4-Hydroxy)phenoxy-2-(1-hydroxy-2-methylbut-1-yl)benzo[b]thiophene;
3(4-Hydroxy)phenoxy-2-(1-hydroxy-3-methylbut-1-yl)benzo[b]thiophene;
3(4-Hydroxy)phenoxy-2-(1-hydroxy-4-methylbut-1-yl)benzo[b]thiophene;
3(4-Hydroxy)phenoxy-2-(1-hydroxy-2-methylprop-1-yl)benzo[b]thiophene;
3(4-Hydroxy)phenoxy-2-(1-hydroxypent-3-ene-1-yl)benzo[b]thiophene;
3(4-Hydroxy)phenoxy-2-(1-hydroxyhex-2,4-diene-1-yl)benzo[b]thiophene;
3(4-Benzyloxy)phenoxy-2-(1-hydroxy-n-pentyl-1-yl)-6-methoxybenzo[b]thiophene;
3(4-Hydroxy)phenoxy-2-(1-hydroxy-2-methylbut-1-yl)-6-methoxybenzo[b]thiophene;
3(4-Benzyloxy)phenoxy-2-(1-hydroxy-3-methylbut-1-yl)-6-methoxybenzo[b]thiophene;
3(4-Hydroxy)phenoxy-2-(1-hydroxy-4-methylbut-1-yl)-6-methoxybenzo[b]thiophene;
3(4-Benzyloxy)phenoxy-2-(1-hydroxy-2-methylprop-1-yl)-6-methoxybenzo[b]thiophene;
3(4-Hydroxy)phenoxy-2-(1-hydroxypent-3-ene-1-yl)-6-methoxybenzo[b]thiophene; and
3(4-Benzyloxy)phenoxy-2-(1-hex-2,4-dieneyl)-6-methoxybenzo[b]thiophene.

\* \* \* \* \*